US011638556B2

(12) United States Patent
Wu et al.

(10) Patent No.: US 11,638,556 B2
(45) Date of Patent: May 2, 2023

(54) ESTIMATING CALORIC EXPENDITURE USING HEART RATE MODEL SPECIFIC TO MOTION CLASS

(71) Applicant: Apple Inc., Cupertino, CA (US)

(72) Inventors: Di Wu, San Jose, CA (US); James Ochs, San Francisco, CA (US); Paige N. Stanley, San Jose, CA (US); Karthik Jayaraman Raghuram, Mountain View, CA (US)

(73) Assignee: Apple Inc., Cupertino, CA (US)

( * ) Notice: Subject to any disclaimer, the term of this patent is extended or adjusted under 35 U.S.C. 154(b) by 310 days.

(21) Appl. No.: 17/033,634

(22) Filed: Sep. 25, 2020

(65) Prior Publication Data

US 2022/0096006 A1    Mar. 31, 2022

(51) Int. Cl.
*A61B 5/00*        (2006.01)
*A61B 5/0205*      (2006.01)
(Continued)

(52) U.S. Cl.
CPC .......... *A61B 5/4866* (2013.01); *A61B 5/0205* (2013.01); *A61B 5/1121* (2013.01); *A61B 5/1123* (2013.01); *A61B 5/7203* (2013.01); *A61B 5/7246* (2013.01); *A61B 5/7264* (2013.01); *A61B 5/7275* (2013.01); *A61B 5/7278* (2013.01); *G16H 10/60* (2018.01); *G16H 20/30* (2018.01); *G16H 40/67* (2018.01); *G16H 50/30* (2018.01);
(Continued)

(58) Field of Classification Search
CPC ... A61B 5/4866; A61B 5/0205; A61B 5/1121; A61B 5/1123; A61B 5/7203; A61B 5/7246; A61B 5/7264; A61B 5/7275; A61B 5/7278; A61B 5/02438; A61B 5/14542; A61B 5/4884; G16H 20/30; G16H 40/67; G16H 10/60; G16H 50/30
See application file for complete search history.

(56) References Cited

U.S. PATENT DOCUMENTS

| 9,848,823 B2* | 12/2017 | Raghuram | A61B 5/7246 |
| 2015/0122018 A1* | 5/2015 | Yuen | A61B 5/4812 73/514.01 |

(Continued)

*Primary Examiner* — Kyle R Quigley
*Assistant Examiner* — Xiuqin Sun
(74) *Attorney, Agent, or Firm* — Fish & Richardson P.C.

(57) ABSTRACT

Embodiments are disclosed for estimating caloric expenditure using a heart rate model specific to a motion class. In an embodiment, a method comprises: obtaining acceleration and rotation rate from motion sensors of a wearable device; determining a vertical component of inertial acceleration and a vertical component of rotational acceleration from the acceleration and rotation rate, respectively; determining a magnitude of the rotation rate; determining a correlation between the inertial vertical acceleration component and rotational acceleration; determining a percentage of motion outside a dominant plane of motion; predicting a motion class based on a motion classification model that takes as input the motions, correlation and percentage; determining a likelihood the user is walking; in accordance with determining that the user is likely not walking, configuring a heart rate model based on the predicted motion class; and estimating, using the configured heart rate model, a caloric expenditure of the user.

18 Claims, 8 Drawing Sheets

(51) Int. Cl.
*A61B 5/11* (2006.01)
*G16H 20/30* (2018.01)
*G16H 40/67* (2018.01)
*G16H 50/30* (2018.01)
*G16H 10/60* (2018.01)
*A61B 5/024* (2006.01)
*A61B 5/145* (2006.01)

(52) U.S. Cl.
CPC ....... *A61B 5/02438* (2013.01); *A61B 5/14542* (2013.01); *A61B 5/4884* (2013.01)

(56) References Cited

U.S. PATENT DOCUMENTS

| | | | |
|---|---|---|---|
| 2016/0058371 A1* | 3/2016 | Singh Alvarado | A61B 5/725 600/483 |
| 2016/0081620 A1* | 3/2016 | Narayanan | G01C 22/006 600/595 |
| 2018/0055439 A1* | 3/2018 | Pham | A61B 5/0205 |
| 2019/0008394 A1* | 1/2019 | Rao | G16H 50/30 |
| 2019/0090756 A1* | 3/2019 | Lu | A61B 5/02438 |

\* cited by examiner

ESTIMATING CALORIC EXPENDITURE USING HEART RATE MODEL SPECIFIC TO MOTION CLASS

TECHNICAL FIELD

This disclosure relates generally to activity monitoring using wearable devices.

BACKGROUND

The metabolic equivalent of task (MET) is defined as a ratio of the rate of energy expended by an individual during physical activity to the rate of energy expended by the user at rest (referred to as the resting metabolic rate (RMR)). Many studies have shown that the conventional 1-MET baseline overestimates actual resting oxygen consumption and energy expenditures by about 20% to 30% on average. Therefore, an accurate calculation of MET for a specific individual requires data specific to the user and the activity.

Modern wearable devices (e.g., smart watches, fitness bands) are often used by individuals during fitness activities to determine their caloric expenditure during the fitness activity. Some wearable devices include inertial sensors (e.g., accelerometers, angular rate sensors) that are used to estimate a work rate (WR) based MET for the user wearing the device. Some wearable devices include a heart rate (HR) sensor that provides HR data that can be used with user estimated maximal oxygen consumption ($VO_2Max$) and other data (e.g., users weight, age) to estimate HR based MET.

Because studies have shown that upper limb exercise leads to higher heart rate than lower limb motion there is a need for different HR models for upper limb exercise and lower limb exercise and thus a need to detect upper and lower limb motion.

SUMMARY

Embodiments are disclosed for estimating caloric expenditure using a heart rate model specific to a motion class.

In an embodiment, a method comprises: obtaining, using one or more processors, acceleration and rotation rate from motion sensors of a wearable device worn on a limb of a user while the user is engaged in a physical activity; determining, using the one or more processors, a vertical component of inertial acceleration and a vertical component of rotational acceleration from the acceleration and rotation rate, respectively; determining, using the one or more processors, a magnitude of the rotation rate; determining, using the one or more processors, a correlation between the vertical component of inertial acceleration and the vertical component of rotational acceleration rate; determining, using the one or more processors, a percentage of motion outside a dominant plane of motion; predicting, using the one or more processors, a motion class based on a motion classification model that takes as input the vertical components of inertial acceleration and rotational acceleration, the magnitude of rotation rate, the correlation between the vertical component of the inertial acceleration and the vertical component of rotational acceleration and the percentage of motion outside the dominant motion plane; determining, using the one or more processors, a likelihood the user is walking; in accordance with determining that the user is likely not walking, configuring, using the one or more processors, a heart rate model based on the predicted motion class; and estimating, using the configured heart rate model, a caloric expenditure of the user.

In an embodiment, determining, using the one or more processors, a likelihood that the user is walking, further comprises: obtaining, from a digital pedometer, a step count; determining an arm pose of the user; and determining whether or not the user is walking based on the step count and arm pose.

In an embodiment, the motion classification model outputs one of three possible classes: arm only motion, with body motion and other motion.

In an embodiment, the motion classification model has two parts: a first part that uses a logistic regression model with vertical acceleration, vertical component of the rotational acceleration, and correlation between the two acceleration to predict a likelihood of arm motion only, and a second part that detects a body component in the motion with a moderate likelihood from the logistic regression model, wherein if the percentage of motion outside of the dominant plane is above a threshold and the inertial vertical acceleration is within an expected range of body motion, the classification is with body motion.

In an embodiment, configuring, using the one or more processors, a heart rate model based on the predicted motion class, further comprises: determining a first caloric expenditure based on a heart rate model; obtaining a scale factor based on the predicted motion class; and scaling the first caloric expenditure by the scale factor to get a second caloric expenditure specific to the motion class.

In an embodiment, the predicted motion class is one of a plurality of motion classes including arm only motion, with body motion and other motion.

In an embodiment, determining a first caloric expenditure based on a heart rate model, further comprises: obtaining the user's age; obtaining the user's heart rate from a heart rate sensor embedded in or attached to the wearable device; obtaining the user's maximal oxygen uptake ($VO_2Max$); and determining the first caloric expenditure based on the heart rate model with the user's age, the users heart rate and the user's $VO_2Max$ as inputs into the heart rate model. In the case where the user's age and $VO_2Max$ are not available a default caloric expenditure is used.

In an embodiment, the rotation rate is compensated for drift.

In an embodiment, the dominant plane of motion is determined using principle component analysis (PCA) of a crown vector of the wearable device, where the dominant plane is determined by first and second PCA components and the percentage of motion outside of the dominant plane is a fraction of a variance in a third PCA component, which is a ratio of the variance in the third component and a total variance.

In an embodiment, a system comprises: one or more processors; memory storing instructions that when executed by the one or more processors, cause the one or more processors to perform operations comprising: obtaining acceleration and rotation rate from motion sensors of a wearable device worn on a limb of a user while the user is engaged in a physical activity; determining a vertical component of inertial acceleration and a vertical component of rotational acceleration from the acceleration and rotation rate, respectively; determining a magnitude of the rotation rate; determining a correlation between the inertial vertical acceleration component and rotational acceleration; determining a percentage of motion outside a dominant plane of motion; predicting a motion class based on a motion classification model that takes as input the vertical components of inertial acceleration and rotational acceleration, the magnitude of rotation rate, the correlation between the vertical components of the inertial acceleration and rotational acceleration and the percentage of motion outside the dominant motion plane; determining a likelihood that the user is walking; in accordance with determining that the user is likely not walking, configuring a heart rate model based on the predicted motion class; and estimating, using the configured heart rate model, a caloric expenditure of the user.

Other embodiments can include an apparatus, computing device and non-transitory, computer-readable storage medium.

The details of one or more implementations of the subject matter are set forth in the accompanying drawings and the description below. Other features, aspects and advantages of the subject matter will become apparent from the description, the drawings and the claims.

DETAILED DESCRIPTION

Problem Statement

Figure 1A:
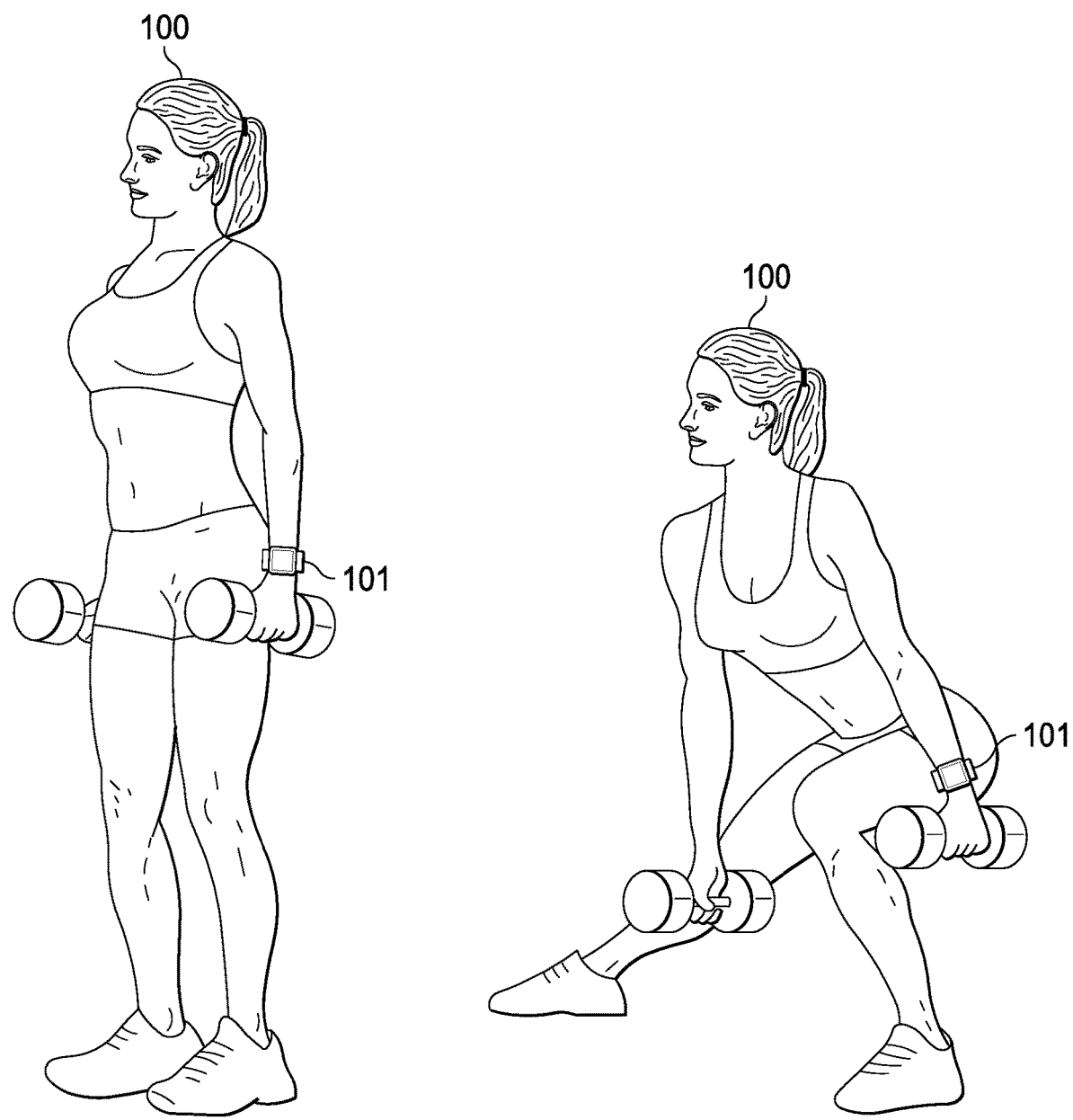
FIG. 1A illustrates a compound exercise where the participant is lifting dumbbells while performing side squats, according to an embodiment.
Figure 7:
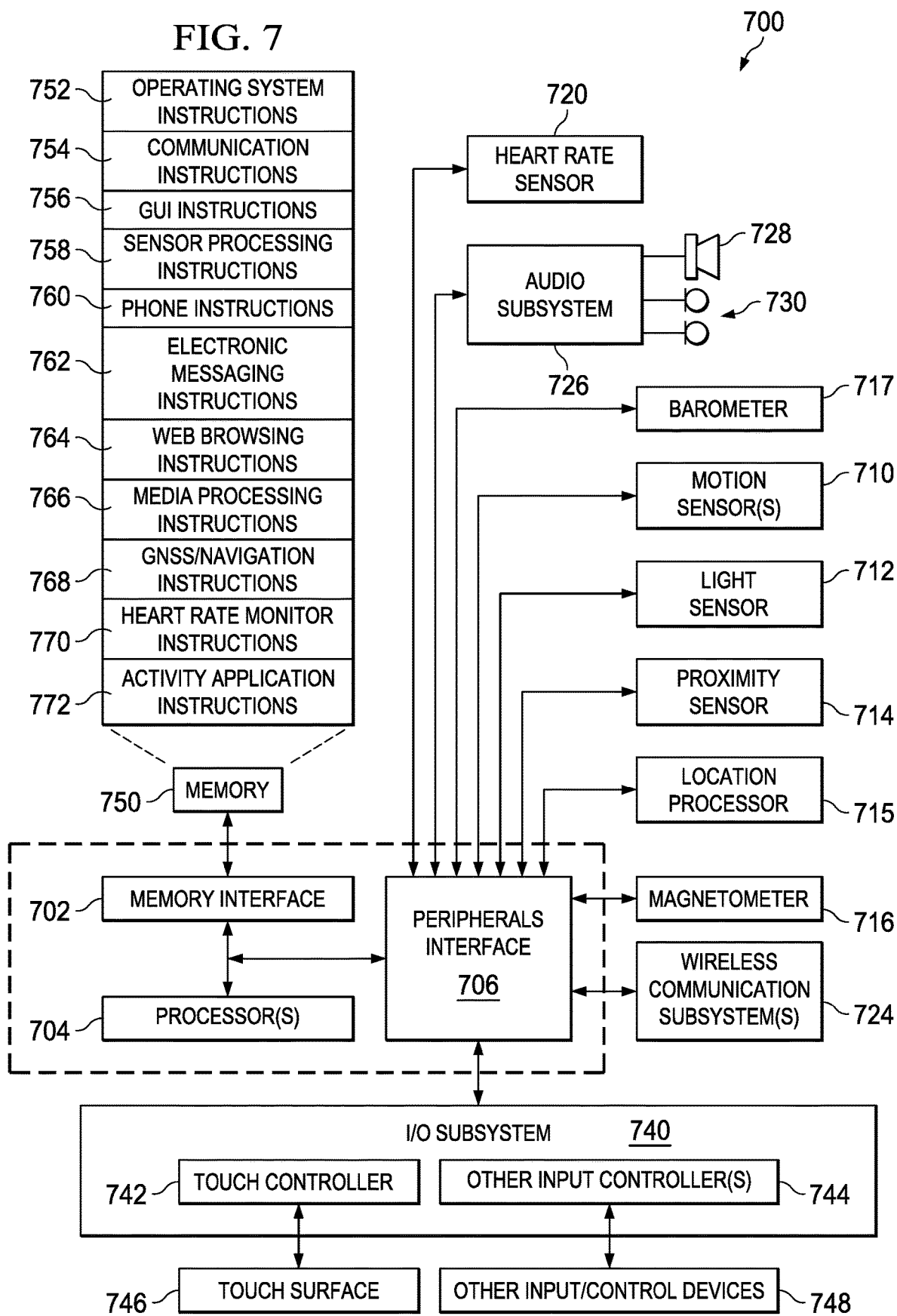
FIG. 7 is example wearable device architecture for a wearable device implementing the features and operations described in reference to FIGS. 1-6.

FIG. 1A illustrates a compound exercise where the participant is lifting dumbbells while performing side squats, according to an embodiment. In this example, wearable device 101 is worn on the wrist of participant 100. Wearable device 101 can be, for example, a smart watch or fitness band or any other device that can measure accelerations and rotation rate. In an embodiment, wearable device 101 can have an architecture as shown in FIG. 7, which includes a 3-axis MEMs accelerometer for measuring acceleration and a 3-axis MEMS gyro for measuring angular rates. During the exercise, participant 100 is lifting dumbbells and squatting from side-to-side. The lifting of the dumbbells is an example of upper limb motion and the side squats are an example of lower limb motion. Using an HR model designed for whole body workouts (like walking and running) would overestimate the calorie expenditure of the user when the user engages only their upper limb in the exercise and their HR increases. Accordingly, it is desirable to use different HR models for upper limb motion and lower limb motion, which requires that the upper limb motion be distinguished from the lower limb motion so that the appropriate HR model is used to determine the user's total calorie expenditure for the exercise.

Figure 1B:
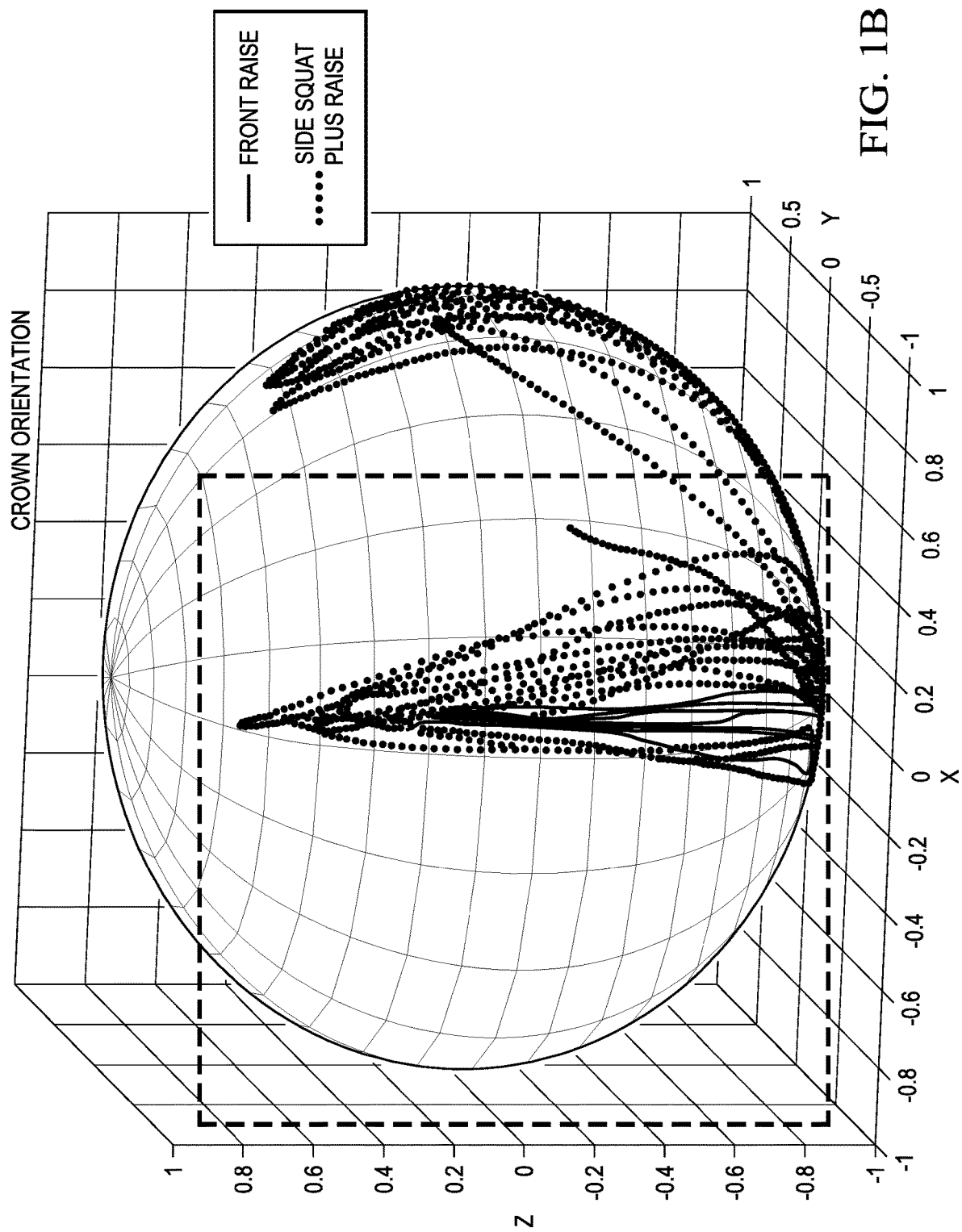
FIG. 1B illustrates three-dimensional (3D) motion in a wearable device body frame for side squat plus arm raise and front arm raise, according to an embodiment.
Figure 2A:
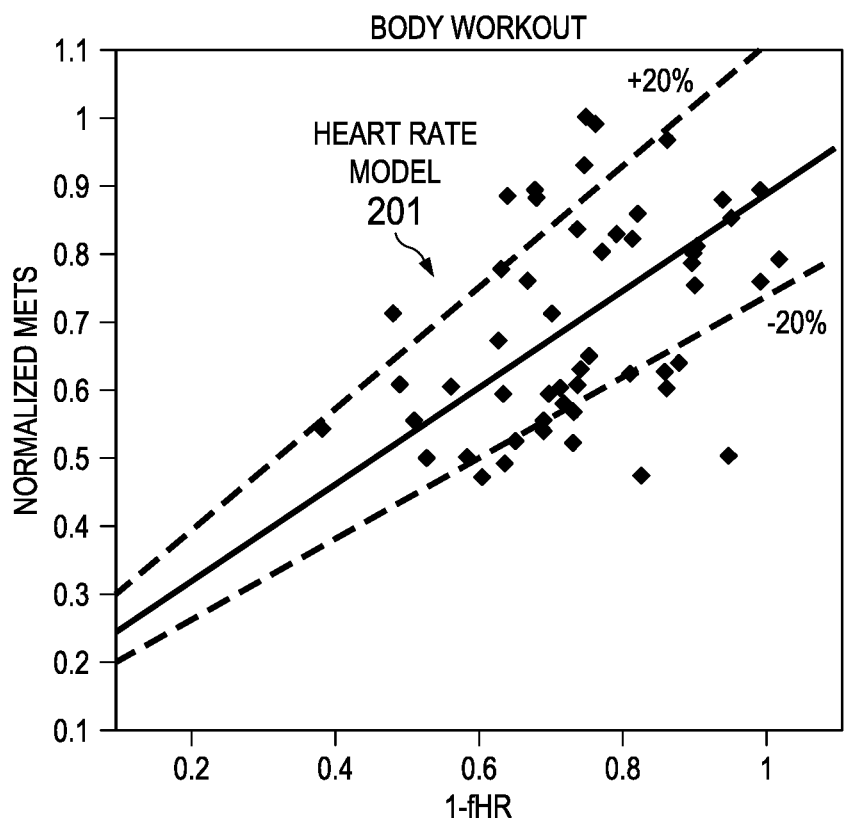
FIG. 2A is a scatter plot illustrating normalized METs versus 1-fHR for a body workout, according to an embodiment.

As can be observed from FIG. 1B, when using solely the upper body to perform front raises, there is a single dominant plane of motion. When performing the compound motion of side squats and front raises using both the upper and lower body simultaneously, the wearable device orientation takes a more complex trajectory and there is not one clear dominant plane of motion. Note that the signal/peaks appearing on the right outside of the boxed region are from side raises FIG. 2A is a scatter plot illustrating normalized METs versus 1-fHR for a body only workout, according to an embodiment. For this plot 50 data points were plotted for a 0.5 min to 1 min non-anaerobic exercise segment with stable METs (Note: NormalizedMETS=METs/VO$_2$Max). Linear regression analysis shows that HR model 201 (represented by the straight line) used to compute the METs is valid for body only workouts because most of the data points fall within the +/−20% linearity uncertainty bound represented by the dashed lines. Note that fHR=(hr_max−hr)/(hr_max−hr_min), where hr=heart rate measurement, hr_max=user's estimated maximum heart rate hr_min=user's estimated minimum heart rate, thus if 1-fHR=0.3, then that is 30% of the way to the maximum heart rate.

Figure 2B:
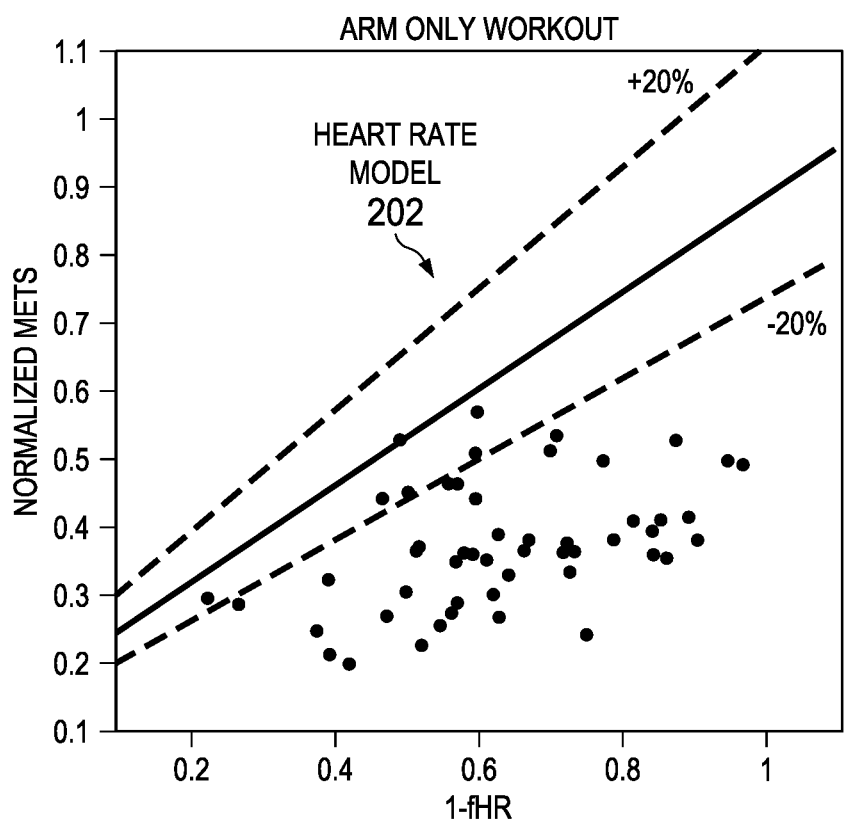
FIG. 2B is a scatter plot illustrating normalized METs versus 1-fHR for an arm only workout, according to an embodiment.

FIG. 2B is a scatter plot illustrating normalized METs versus 1-fHR for an arm only workout, according to an embodiment. For this plot 50 data points were plotted for a 0.5 min to 1 min non-anaerobic exercise segment with stable METs. Linear regression analysis shows that HR model 201 used to compute the METs is not valid for arm only workouts because most of the data points fall outside the +/−20% linearity uncertainty bound represented by the dashed lines.

Accordingly, FIGS. 2A and 2B illustrate that at least two different HR models are needed to accurately calculate HR based METs for compound workouts: one for workouts with body motion and one for workouts with arm only motion. Some examples of arm only workouts include but are not limited to: ball down curl press, bicep curl, bicep curl with rotation, front raise, front and lateral raise, lat pulldown, lateral raise, low chest fly, rear delt pull, upper body row and up right row. Some examples of body motion workouts include but are not limited to: lat pull down with squat, lunges, lunges plus row, side squat lunges, side squat plus raise, squat, squat with ball and squat with lunges. Examples of exercises that are not arm only motion or body motion include but are not limited to: plank walkout, pushup with side plank and Russian twists.

System Overview

Figure 3:
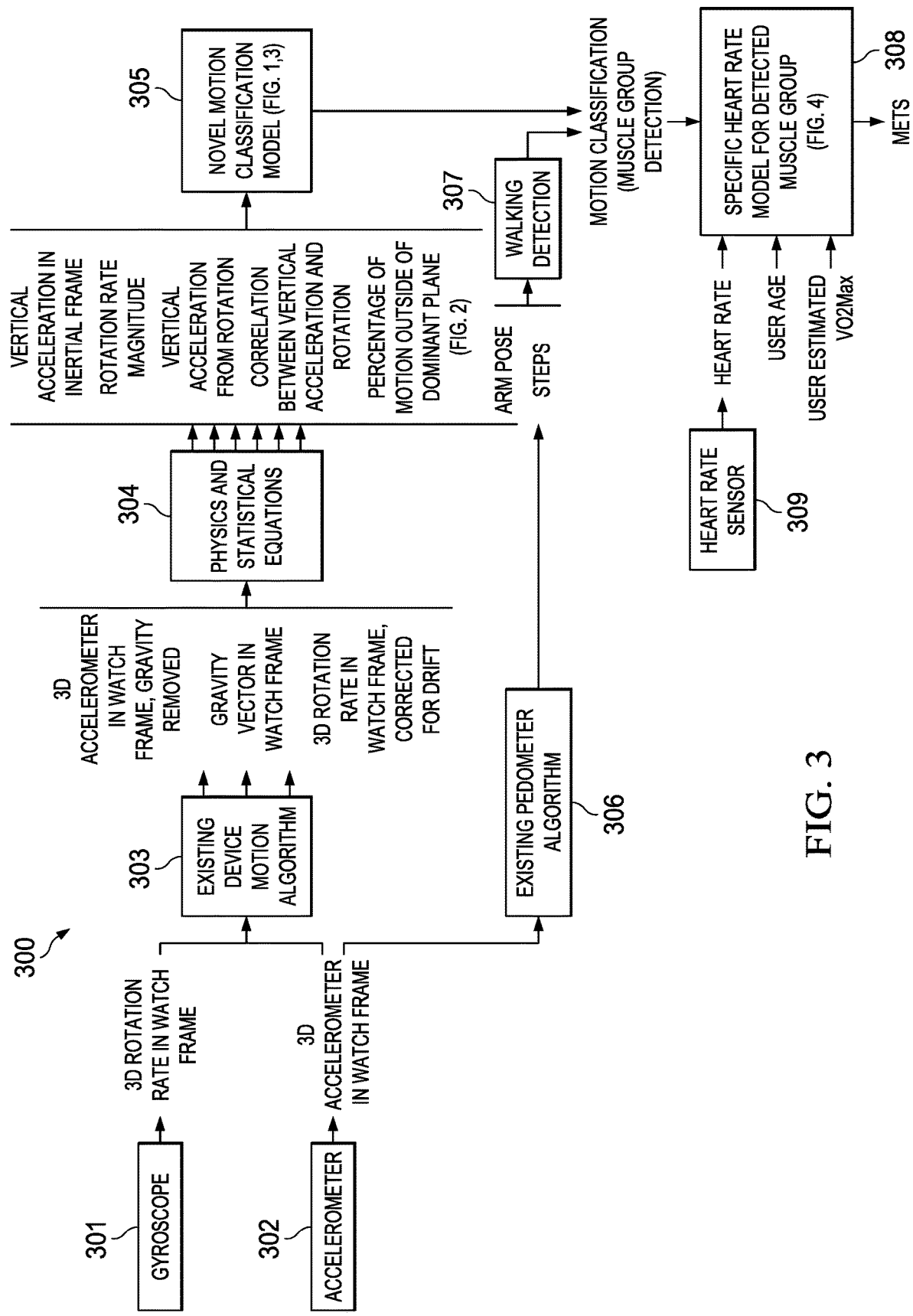
FIG. 3 is a block diagram of a system for determining caloric expenditure using a HR rate model specific to motion class, according to an embodiment.

FIG. 3 illustrates a system 300 for determining caloric expenditure using a HR rate model specific to a motion class, according to an embodiment. System 300 can be implemented in a wearable device, such as a smartwatch or fitness band worn on a wrist of a user during a physical activity, such as a workout. Although the embodiments that follow describe exercises, the disclosed embodiments are applicable to any physical activity that where an caloric expenditure is desired.

In an embodiment, the wearable device includes motion sensors, such as accelerometer 301 (e.g., a 3-axis MEMS accelerometer) and angular rate sensor 302 (e.g., 3-axis MEMS gyro) that provide a three-dimensional (3D) acceleration vector and 3D rotation rate vector in a body frame of the wearable device, respectively. The 3D acceleration and rotation rate vectors are input into motion processor 303, which computes and outputs a 3D acceleration vector with gravity removed, a gravity vector and a 3D rotation rate vector that is compensated for drift.

The output of motion processor 303 is input into physics/statistics processor 304, which computes and outputs a vertical component of inertial acceleration in an inertial world coordinate frame (hereinafter, referred to as "inertial frame"), a rotation rate magnitude, a vertical component of rotational acceleration in the inertial coordinate frame due to the rotation of the user's limb and a correlation coefficient representing the correlation between the vertical component of translational acceleration and the vertical component of rotational acceleration.

In an embodiment, physics/statistics processor 304 uses a coordinate transformation (e.g., a direction cosine matrix or quaternion) that uses yaw, pitch and roll angles derived from the 3D rotation rate to transform the 3D acceleration vector (with gravity removed) from the wearable device body frame to the inertial frame, where the vertical component of inertial acceleration is normal to the Earth surface. The rotation magnitude is computed by taking the Euclidean norm of the rotation rate vector. In an embodiment, the correlation coefficient is directly calculated using the Pearson correlation equation, between inertial vertical acceleration and the inertial vertical rotational acceleration. Also computed by physics/statistics processor 304 is a percentage of motion outside the dominant plane and the user's limb pose (e.g., arm pose).

In an embodiment, the dominant plane of motion is determined using principle component analysis (PCA) of a crown vector of the wearable device per measurement epoch. The first and second principal components characterize the dominant plane. The third principal component represents motion outside the dominant plane. The eigenvalues of each principal component represent the magnitude of motion in the direction of its respective component. The fraction of motion outside the dominant plane is quantified by a ratio of the third eigenvalue to the L1 norm (sum of absolute values) of all three eigenvalues. In an embodiment, the user's arm pose is defined by the angle between the crown vector and the horizontal direction (the direction perpendicular to gravity).

The vertical component of inertial acceleration, rotation rate magnitude, the vertical component of rotational acceleration, the correlation between the vertical component of inertial acceleration and the vertical component of rotational acceleration, the percentage of motion outside the dominant plane and the arm pose are inputs into motion classification model 305, which predicts a motion class based on the input. In an embodiment, motion classification model 305 predicts one of three motion classes: with body motion, arm only motion and other, as described in further detail in reference to FIG. 4.

Figure 4:
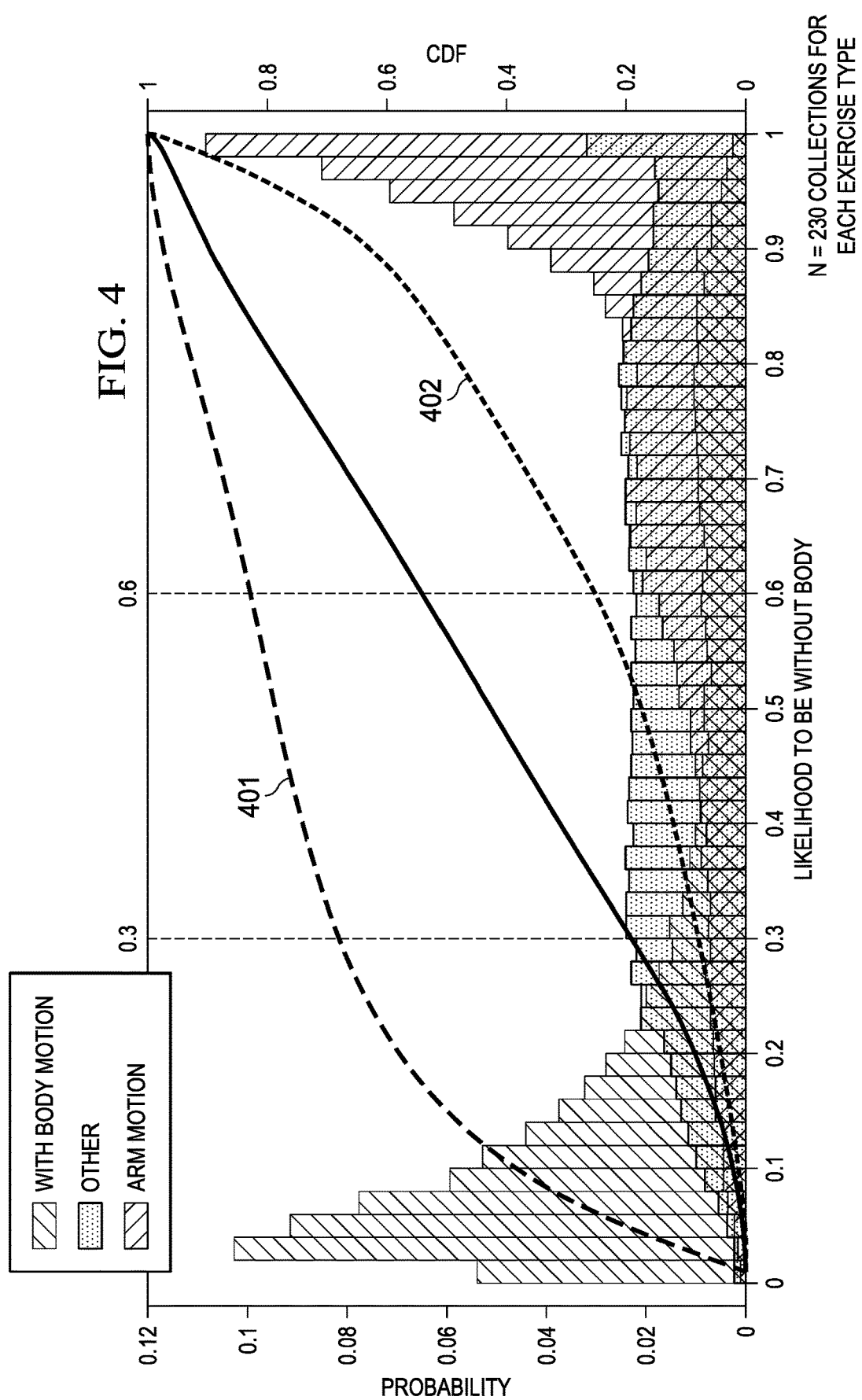
FIG. 4 illustrates a motion classification model, according to an embodiment.

In an embodiment, motion classification model 305 has two parts: a logistic regression with vertical acceleration, vertical component of the rotational acceleration, and correlation between the two aforementioned accelerations. The output from the logistic regression model is the likelihood to be without body motion (arm motion only) workout, as illustrated by FIG. 4. The second part of motion classification model 305 is to further detect the body component in the motion with a moderate likelihood from the logistic regression model. If the percentage of motion outside of the dominant plane is above a threshold and the inertial vertical acceleration is in expected range of body motion, the classification would be with body.

Other embodiments can include more or fewer motion classes. Any suitable motion classification model can be used to predict motion classes, including machine learning algorithms.

FIG. 4 shows a histogram with probabilities and corresponding cumulative distribution functions for body motion and arm only motion, according to an embodiment. The probabilities and CDFs are represented by the y-axis and likelihoods to be without (w/o) body motion are represented by the x-axis. CDF 401 is associated with the w/body motion portion of the histogram and CDF 402 is associated with the arm only motion portion of the histogram. The probabilities of the predicted motion classes were estimated from 230 collections of exercises with body motion and arm only motion. As shown in FIG. 4, if there is a likelihood of 0.3 or lower the detected motion is w/o body motion, the motion is classified/labeled as "w/body motion." If the likelihood is 0.8 or above, the motion is classified/labeled as "arm only motion." Otherwise, the motion is classified/labeled as "other" class. The three classes shown are based on a true label. The histogram of FIG. 4 shows that the likelihood from the logistic regression model provides a good separation between the classes, especially between the w/o body motion and the w/body motion classes. Thresholds are set based on this separation. For example, as shown in the plot, if the likelihood is below 0.3, the motion is likely to be w/body motion, and less likely to be w/o body motion.

Figure 5C:
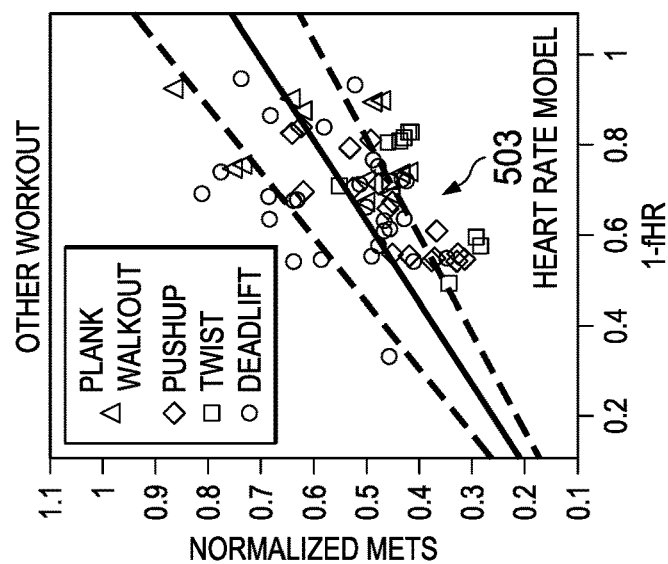
FIG. 5C is a scatter plot illustrating normalized METs versus 1-fHR for other types of workouts, according to an embodiment.
Figure 5B:
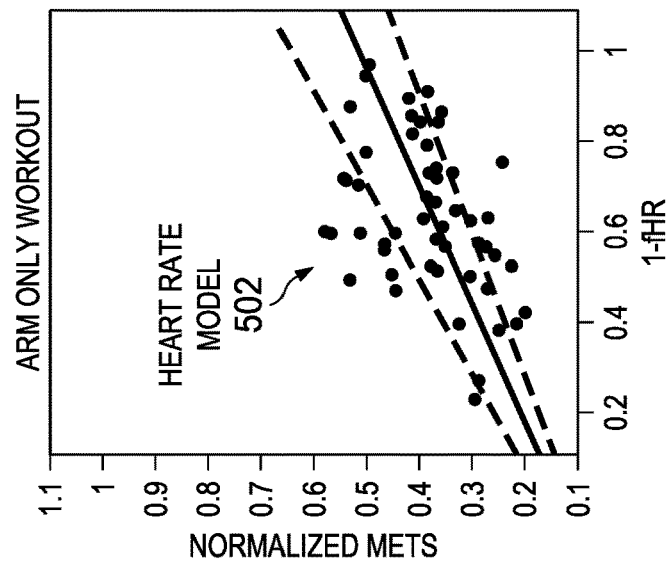
FIG. 5B is a scatter plot illustrating normalized METs versus 1-fHR for an arm only workout, according to an embodiment.
Figure 5A:
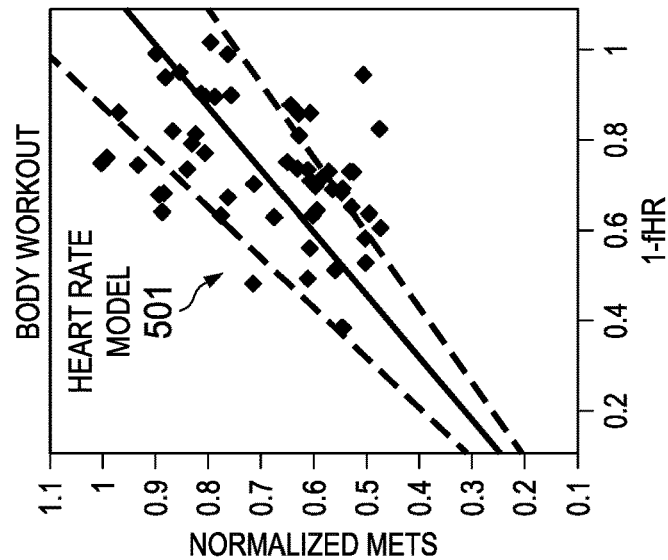
FIG. 5A is a scatter plot illustrating normalized METs versus 1-fHR for a body workout, according to an embodiment.

FIGS. 5A-5C are scatter plots showing linear regression analysis for body workouts, arm only workouts and other workouts, respectively. Each plot includes 50 data points of HR and normalized METS collected via reference devices. The solid lines represent the fitted HR models 502 and 503 are the w/body HR model scaled by a fraction of the engaged muscle size to the big muscle in the leg. In an embodiment, the HR model calculates HR based METS for each class is calculated using Equation [1]:

$$METS_{exercise} = R_{exercise} * f(fHR_{exercise}) * VO_2MAX, \quad [1]$$

where $f(fHR\_exercise)$) is any known HR model that works well for with total body exercise (e.g., running, jogging) and $R_{exercise}$ represents a fraction of the engaged muscle size to the larger muscles in the leg, and is in a range of 0.0 to 1.0, the actual values of which can be determined empirically. By applying Equation [1], the HR based MET values output by the HR model for total body exercise are reduced, thus correcting the overestimate of HR based MET values when the exercise engages only the upper limb or certain exercises that engage abdominals or back muscles.

Referring back to FIG. 3, walking detection processor 307 receives a step count and limb pose. In an embodiment, the step count is provided by digital pedometer 306. Digital pedometer 306 counts steps based on the 3D acceleration vector in the wearable device body frame. For example, digital pedometer 306 can count steps by, for example, counting peaks and/or valleys in a plot of acceleration magnitudes, using frequency spectrum analysis, using machine learning, or any combination of the foregoing or any other suitable digital pedometer algorithm. The step count and limb pose (e.g., the angle of the arm with respect to gravity) are input into walking detector 307, which determines if the user is walking. If walking detector processor 307 detects steps, and at the same time the user's arm is pointing down most of the time, then the motion is detected as w/body and the w/body heart rate model is used. This feature covers the potential cases of the user walking around during exercise.

The motion class and a walking detection signal are input into HR model 308, which is configured according to the motion class. Also input into the HR model 308 is HR data from HR sensor 309, the user's age and the user's estimated $VO_2Max$. In an embodiment, HR sensor 309 measures the user's HR, which is input into HR model 308. In an embodiment, HR sensor 309 is embedded in a wearable device and comprises a number of light emitting diodes (LEDs) paired with photodiodes that can sense light. The LEDs emit light toward a user's body part (e.g., the user's wrist), and the photodiodes measure the reflected light. The difference between the sourced and reflected light is the amount of light absorbed by the user's body. Accordingly, the user's heart beat modulates the reflected light, which can be processed to determine the user's HR. The measured HR can be averaged over time to determine an average HR, which input into HR model 308.

In an embodiment, HR model 308 estimates caloric expenditure (e.g., METs) during steady-state aerobic exercise using a relationship between heart rate and the user's estimated $VO_2MAX$. As previously discussed, HR Model 308 includes three models for different motion classes, as described in reference to FIG. 5. During steady-state aerobic exercise, oxygen is utilized at a relatively consistent rate depending on the intensity of the exercise. There is an observable and reproducible relationship between heart rate and the calories burned from consumed $VO_2$. When workload intensity increases, HR increases and vice versa. If the user's resting HR, maximum HR, user's $VO_2$ MAX and age (and optionally weight for some models) are known, caloric expenditure (METs) can be estimated based on a percentage of the user's maximum HR or a percentage of the user's HR reserve.

In an embodiment, HR model 308 takes as input calibrated $VO_2MAX$ and the user's HR. The calibrated $VO_2$ MAX can be computed using work rate (WR) MET values (which are implicit estimates of $VO_2$) with the user's measured HR data. The output of HR model 308 are HR based MET values. The HR based MET values can be used for any desired purpose, including but not limited to: presentation on a display of the wearable device by a fitness or other application as an estimate of caloric expenditure, sent to another device for display and/or further processing by one or more other applications, stored on the wearable device for subsequent display/processing by one or more applications, or sent to a network-based computer system (the "cloud"), where the HR based MET values can be displayed/processed by other devices connected to the network-based computer system.

In an embodiment, HR based MET values are estimated over successive, non-overlapping intervals of time referred to herein as "epochs." An "epoch" can be x seconds (e.g., 2.56 seconds, corresponding to 256 samples of sensor data sampled at 100 Hz). In an embodiment, the HR based MET can be combined (e.g., averaged) with work rate (WR) based MET values.

Example Process

Figure 6:
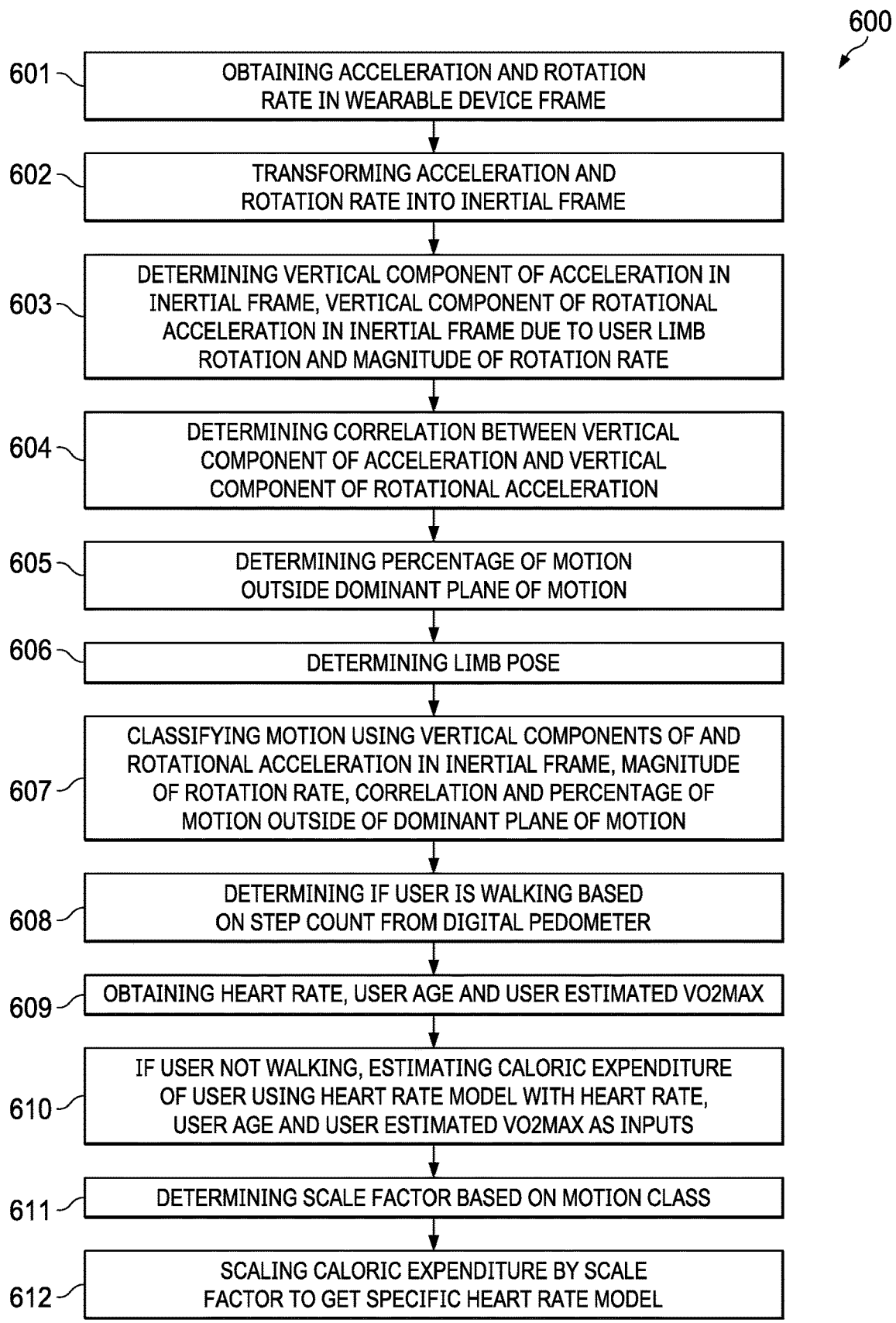
FIG. 6 is a flow diagram of a process of determining caloric expenditure using a HR rate model specific to a motion class, according to an embodiment.

FIG. 6 is a flow diagram of process 600 of determining caloric expenditure using a HR rate model specific to a motion class, according to an embodiment. Process 600 can be implemented using the wearable device architecture 700 disclosed in reference to FIG. 7.

Process 600 includes obtaining acceleration and rotation rate from a wearable device worn on a limb of a user while the user is engaged in a physical activity (601). For example, the wearable device can be a smart watch or fitness band worn on the wrist of the user during a physical activity. Acceleration can be sensed by a 3-axis MEMS accelerometer that outputs a 3D acceleration vector. Rotation rate can be sensed by a 3-axis MEMS gyroscope that outputs a 3D rotation rate vector, which is compensated for drift. In an embodiment, a motion processor computes the 3D acceleration vector with gravity removed, the gravity vector and 3D rotation rate in body frame of the wearable device that is compensated for drift.

Process 600 continues by determining vertical components (Az) of inertial acceleration and rotational acceleration from the 3D acceleration and compensated rotation rate (602). For example, the raw acceleration and rotation rate output by the sensors 301, 302 can be transformed into an inertial world frame, and the vertical component is the motion that moves in a vertical plane normal to the ground. In an embodiment, the rotational acceleration is estimated from the rotation rate and a crown vector (directional vector from elbow to hand in an inertial reference frame) provided by motion processor 303.

Process 600 continues by determining a magnitude of the rotation rate (603). The magnitude can be computed by taking the absolute value of the rotation rate vector output by gyro sensor 302.

Process 600 continues by determining a correlation between the vertical components of the translational and rotational acceleration (604). For example, in additional to translation acceleration there is an additional component of vertical acceleration due to rotation of the user's limb. In an embodiment, the correlation coefficient is calculated directly using a Pearson correlation coefficient.

Process 600 continues by determining a percentage of motion outside a dominant plane of motion from the crown vector, which is the vector of crown direction in an inertial reference frame (605). For example, PCA can be applied to the crown vector, which gives the three independent components in order based on the variance in each. The percentage out of the dominant plane is the ratio of the variance of the third component to the total variance. The third component is perpendicular to the dominant plane determined by the first two components.

Process 600 continues by predicting, using a motion classification model, a motion class label based on the vertical components of inertial acceleration and rotational acceleration, the magnitude of rotation rate, the correlation between the vertical components of the translational and rotational acceleration and the percentage of motion outside the dominant motion plane (606). For example the motion classification model can be a logistic regression model that predicts one of three possible motion classes: "w/body"

motion class, an "arm only" motion class and "other" motion that includes all other types of detected motion, as described in reference to FIG. 4.

Process 600 continues by determining whether or not the user is walking (607). For the user's step count and arm pose can be used to determine whether or not the user is walking. If the user is walking then a generic HR model is used to calculate caloric expenditure based on user's HR, age and estimated VO$_2$Max. If walking is not detected, then a HR model specific to the motion class predicted by motion classification model 305 is used to calculate caloric expenditure.

Process 600 continues by configuring a HR model based on the motion class label and whether (608). For example, while the user is engaged in a physical activity multiple acceleration and rotation rate measurements are taken and the motion is predicted based on the vertical translation and rotational components of acceleration and a correlation between the vertical components. The predicted motion class is then used to select or determine a scale factor that can be applied to caloric generated by a generic HR model, for example, that estimates HR based METs based on the user's HR, the user's age and the user's estimated VO$_2$Max.

Process 600 continues by estimating, using the configured heart rate model, a caloric expenditure of the user (609). For example, the scale factor can be applied to the MET values output by the generic HR model. In an embodiment, caloric expenditure is estimated when the user may be walking and when the user may be standing in place. The walking detection allows "with body" motion to be recovered that may have been missed. For example, if the user is likely to be walking, the "with body" HR model is used. Otherwise, the HR model for the previous motion classification is used, which could be any of arm only, with body, other.

Once the HR based caloric expenditure is calculated it can be used by other applications (e.g., fitness applications) running on the wearable device or another device, displayed on the wearable device or another device, sent to another device through a local area network, ad hoc wireless network or wide area network (e.g., the Internet) to other devices. The HR based METS can be combined (e.g., averaged) with work rate based METs that are computed based on a work rate model that accounts for the amount of energy expended by the user due to the physical activity.

Exemplary Wearable Computer Architecture

FIG. 7 illustrates example wearable device architecture 700 implementing the features and operations described in reference to FIGS. 1-6. Architecture 700 can include memory interface 702, one or more hardware data processors, image processors and/or processors 704 and peripherals interface 706. Memory interface 702, one or more processors 704 and/or peripherals interface 706 can be separate components or can be integrated in one or more integrated circuits.

Sensors, devices and subsystems can be coupled to peripherals interface 706 to provide multiple functionalities. For example, one or more motion sensors 710, light sensor 712 and proximity sensor 714 can be coupled to peripherals interface 706 to facilitate motion sensing (e.g., acceleration, rotation rates), lighting and proximity functions of the wearable device. Location processor 715 can be connected to peripherals interface 706 to provide geo-positioning. In some implementations, location processor 715 can be a GNSS receiver, such as the Global Positioning System (GPS) receiver. Electronic magnetometer 716 (e.g., an integrated circuit chip) can also be connected to peripherals interface 706 to provide data that can be used to determine the direction of magnetic North. Electronic magnetometer 716 can provide data to an electronic compass application. Motion sensor(s) 710 can include one or more accelerometers and/or gyros configured to determine change of speed and direction of movement of the wearable device. Barometer 717 can be configured to measure atmospheric pressure around the mobile device.

Heart rate monitoring subsystem 720 for measuring the heartbeat of a user who is wearing the device on their wrist. In an embodiment, subsystem 720 includes LEDs paired with photodiodes for measuring the amount of light reflected from the wrist (not absorbed by the wrist) to detect a heartbeat.

Communication functions can be facilitated through wireless communication subsystems 724, which can include radio frequency (RF) receivers and transmitters (or transceivers) and/or optical (e.g., infrared) receivers and transmitters. The specific design and implementation of the communication subsystem 724 can depend on the communication network(s) over which a mobile device is intended to operate. For example, architecture 700 can include communication subsystems 724 designed to operate over a GSM network, a GPRS network, an EDGE network, a Wi-Fi™ network and a Bluetooth™ network. In particular, the wireless communication subsystems 724 can include hosting protocols, such that the mobile device can be configured as a base station for other wireless devices.

Audio subsystem 726 can be coupled to a speaker 728 and a microphone 730 to facilitate voice-enabled functions, such as voice recognition, voice replication, digital recording and telephony functions. Audio subsystem 726 can be configured to receive voice commands from the user.

I/O subsystem 740 can include touch surface controller 742 and/or other input controller(s) 744. Touch surface controller 742 can be coupled to a touch surface 746. Touch surface 746 and touch surface controller 742 can, for example, detect contact and movement or break thereof using any of a plurality of touch sensitivity technologies, including but not limited to capacitive, resistive, infrared and surface acoustic wave technologies, as well as other proximity sensor arrays or other elements for determining one or more points of contact with touch surface 746. Touch surface 746 can include, for example, a touch screen or the digital crown of a smart watch. I/O subsystem 740 can include a haptic engine or device for providing haptic feedback (e.g., vibration) in response to commands from processor 704. In an embodiment, touch surface 746 can be a pressure-sensitive surface.

Other input controller(s) 744 can be coupled to other input/control devices 748, such as one or more buttons, rocker switches, thumb-wheel, infrared port and USB port. The one or more buttons (not shown) can include an up/down button for volume control of speaker 728 and/or microphone 730. Touch surface 746 or other controllers 744 (e.g., a button) can include, or be coupled to, fingerprint identification circuitry for use with a fingerprint authentication application to authenticate a user based on their fingerprint(s).

In one implementation, a pressing of the button for a first duration may disengage a lock of the touch surface 746; and a pressing of the button for a second duration that is longer than the first duration may turn power to the mobile device on or off. The user may be able to customize a functionality of one or more of the buttons. The touch surface 746 can, for example, also be used to implement virtual or soft buttons.

In some implementations, the mobile device can present recorded audio and/or video files, such as MP3, AAC and MPEG files. In some implementations, the mobile device can include the functionality of an MP3 player. Other input/output and control devices can also be used.

Memory interface 702 can be coupled to memory 750. Memory 750 can include high-speed random access memory and/or non-volatile memory, such as one or more magnetic disk storage devices, one or more optical storage devices and/or flash memory (e.g., NAND, NOR). Memory 750 can store operating system 752, such as the iOS operating system developed by Apple Inc. of Cupertino, Calif. Operating system 752 may include instructions for handling basic system services and for performing hardware dependent tasks. In some implementations, operating system 752 can include a kernel (e.g., UNIX kernel).

Memory 750 may also store communication instructions 754 to facilitate communicating with one or more additional devices, one or more computers and/or one or more servers, such as, for example, instructions for implementing a software stack for wired or wireless communications with other devices. Memory 750 may include graphical user interface instructions 756 to facilitate graphic user interface processing; sensor processing instructions 758 to facilitate sensor-related processing and functions; phone instructions 760 to facilitate phone-related processes and functions; electronic messaging instructions 762 to facilitate electronic-messaging related processes and functions; web browsing instructions 764 to facilitate web browsing-related processes and functions; media processing instructions 766 to facilitate media processing-related processes and functions; GNSS/Location instructions 768 to facilitate generic GNSS and location-related processes and instructions; and heart rate instructions 770 to facilitate hear rate measurements. Memory 750 further includes activity application (e.g., a fitness application) instructions for performing the features and processes described in reference to FIGS. 1-6.

Each of the above identified instructions and applications can correspond to a set of instructions for performing one or more functions described above. These instructions need not be implemented as separate software programs, procedures, or modules. Memory 750 can include additional instructions or fewer instructions. Furthermore, various functions of the mobile device may be implemented in hardware and/or in software, including in one or more signal processing and/or application specific integrated circuits.

The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., SWIFT, Objective-C, C#, Java), including compiled or interpreted languages, and it can be deployed in any form, including as a stand-alone program or as a module, component, subroutine, a browser-based web application, or other unit suitable for use in a computing environment.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

As described above, some aspects of the subject matter of this specification include gathering and use of data available from various sources to improve services a mobile device can provide to a user. The present disclosure contemplates that in some instances, this gathered data may identify a particular location or an address based on device usage. Such personal information data can include location-based data, addresses, subscriber account identifiers, or other identifying information.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

In the case of advertisement delivery services, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publicly available information.

What is claimed is:

1. A method comprising:
   measuring, using one or more processors, acceleration and rotation rate using motion sensors of a wearable device worn on a limb of a user while the user is engaged in a physical activity;
   determining, using the one or more processors, a vertical component of inertial acceleration and a vertical component of rotational acceleration from the acceleration and rotation rate, respectively;
   determining, using the one or more processors, a magnitude of the rotation rate;
   determining, using the one or more processors, a correlation between the vertical component of inertial acceleration and the vertical component of rotational acceleration;
   determining, using the one or more processors; a percentage of motion outside a dominant plane of motion;
   predicting, using the one or more processors, a motion class based on a motion classification model that takes as input the vertical components of inertial acceleration and rotational acceleration, the magnitude of rotation rate, the correlation between the vertical components of the inertial acceleration and rotational acceleration and the percentage of motion outside the dominant motion plane;
   determining, using the one or more processors, a likelihood that the user is walking;
   in accordance with determining that the user is likely not walking,
      configuring, using the one or more processors, a heart rate model based on the predicted motion class; and
      estimating, using the configured heart rate model, a caloric expenditure of the user.

2. The method of claim 1, wherein determining, using the one or more processors, a likelihood the user is walking, further comprises:
   obtaining, from a digital pedometer, a step count;
   determining an arm pose of the user; and
   determining whether or not the user is walking based on the step count and arm pose.

3. The method of claim 1, wherein the motion classification model outputs one of three possible classes: arm only motion, with body motion and other motion.

4. The method of claim 3, wherein the motion classification model has two parts: a first part that uses a logistic regression model with vertical acceleration, vertical component of the rotational acceleration, and correlation between the two acceleration to predict a likelihood of arm motion only, and a second part that detects a body component in the motion with a moderate likelihood from the logistic regression model, wherein if the percentage of motion outside of the dominant plane is above a threshold and the inertial vertical acceleration is within an expected range of body motion, the classification is with body motion.

5. The method of claim 1, wherein configuring, using the one or more processors, a heart rate model based on the predicted motion class, further comprises:
   determining a first caloric expenditure based on a heart rate model; and
   obtaining a scale factor based on the predicted motion class; and
   scaling the first caloric expenditure by the scale factor to get a second caloric expenditure specific to the motion class.

6. The method of claim 5, wherein the predicted motion class is an arm only motion class and the heart rate model is an arm only heart rate model.

7. The method of claim 5, wherein determining a first caloric expenditure based on a heart rate model, further comprises:
   obtaining the user's age;
   obtaining the user's heart rate from a heart rate sensor embedded in or attached to the wearable device;
   obtaining the user's maximal oxygen uptake ($VO_2Max$); and
   determining the first caloric expenditure based on the heart rate model with the user's age, the users heart rate and the user's $VO_2Max$ as inputs into the heart rate model.

8. The method of claim 1, wherein the rotation rate is compensated for drift.

9. The method of claim 1, wherein the dominant plane of motion is determined using principle component analysis (PCA) of a crown vector of the wearable device, where the dominant plane is determined by first and second PCA components and the percentage of motion outside of the dominant plane is a fraction of a variance in a third PCA component, which is a ratio of the variance in the third component and a total variance.

10. A system comprising:
    motion sensors;
    one or more processors;
    memory storing instructions that when executed by the one or more processors, cause the one or more processors to perform operations comprising:
       measuring acceleration and rotation rate using motion sensors of a wearable device worn on a limb of a user while the user is engaged in a physical activity;
       determining a vertical component of inertial acceleration and a vertical component of rotational acceleration from the acceleration and rotation rate, respectively;
       determining a magnitude of the rotation rate;
       determining a correlation between the inertial vertical acceleration component and rotational acceleration;
       determining a percentage of motion outside a dominant plane of motion;
       predicting a motion class based on a motion classification model that takes as input the vertical components of inertial acceleration and rotational acceleration, the magnitude of rotation rate, the correlation between the vertical components of the inertial acceleration and rotational acceleration and the percentage of motion outside the dominant motion plane;
       determining a likelihood that the user is walking;
       in accordance with determining that the user is likely not walking,
          configuring a heart rate model based on the predicted motion class; and estimating, using the configured heart rate model, a caloric expenditure of the user.

11. The system of claim 10, wherein determining, using the one or more processors, a likelihood the user is walking, further comprises:
obtaining, from a digital pedometer, a step count;
determining an arm pose of the user; and
determining whether or not the user is walking based on the step count and arm pose.

12. The system of claim 10, wherein the motion classification model outputs one of three possible classes: arm only motion, with body motion and other motion.

13. The system of claim 12, wherein the motion classification model has two parts: a first part that uses a logistic regression model with vertical acceleration, vertical component of the rotational acceleration, and correlation between the two acceleration to predict a likelihood of arm motion only, and a second part that detects a body component in the motion with a moderate likelihood from the logistic regression model, wherein if the percentage of motion outside of the dominant plane is above a threshold and the inertial vertical acceleration is within an expected range of body motion, the classification is with body motion.

14. The system of claim 10, wherein configuring, using the one or more processors, a heart rate model based on the predicted motion class, further comprises:
determining a first caloric expenditure based on a heart rate model; and
obtaining a scale factor based on the predicted motion class; and
scaling the first caloric expenditure by the scale factor to get a second caloric expenditure specific to the motion class.

15. The system of claim 14, wherein the predicted motion class is an arm only motion class and the heart rate model is an arm only heart rate model.

16. The system of claim 14, wherein determining a first caloric expenditure based on a heart rate model, further comprises:
obtaining the user's age;
obtaining the user's heart rate from a heart rate sensor embedded in or attached to the wearable device;
obtaining the user's maximal oxygen uptake ($VO_2Max$); and
determining the first caloric expenditure based on the heart rate model with the user's age, the users heart rate and the user's $VO_2Max$ as inputs into the heart rate model.

17. The system of claim 10, wherein the rotation rate is compensated for drift.

18. The system of claim 10, wherein the dominant plane of motion is determined using principle component analysis (PCA) of a crown vector of the wearable device, where the dominant plane is determined by first and second PCA components and the percentage of motion outside of the dominant plane is a fraction of a variance in a third PCA component, which is a ratio of the variance in the third component and a total variance.

* * * * *

UNITED STATES PATENT AND TRADEMARK OFFICE
CERTIFICATE OF CORRECTION

| | | |
|---|---|---|
| PATENT NO. | : 11,638,556 B2 | Page 1 of 1 |
| APPLICATION NO. | : 17/033634 | |
| DATED | : May 2, 2023 | |
| INVENTOR(S) | : Di Wu et al. | |

It is certified that error appears in the above-identified patent and that said Letters Patent is hereby corrected as shown below:

In the Claims

Column 13, Line 29, In Claim 1, delete "processors;" and insert -- processors, --.

Signed and Sealed this
Twenty-seventh Day of June, 2023

*Katherine Kelly Vidal*

Katherine Kelly Vidal
*Director of the United States Patent and Trademark Office*